(12) United States Patent
Xu

(10) Patent No.: US 9,610,049 B2
(45) Date of Patent: Apr. 4, 2017

(54) AUTOMATIC DETECTION OF PATIENT BODY PROFILE AND INTELLIGENT POSITIONING OF PATIENT

(71) Applicant: GE MEDICAL SYSTEMS GLOBAL TECHNOLOGY COMPANY, LLC, Waukesha, WI (US)

(72) Inventor: Huijun Xu, Beijing (CN)

(73) Assignee: General Electric Company, Schenectady, NY (US)

( * ) Notice: Subject to any disclaimer, the term of this patent is extended or adjusted under 35 U.S.C. 154(b) by 396 days.

(21) Appl. No.: 14/169,188

(22) Filed: Jan. 31, 2014

(65) Prior Publication Data

US 2014/0210470 A1   Jul. 31, 2014

Related U.S. Application Data

(63) Continuation of application No. 14/167,591, filed on Jan. 29, 2014.

(30) Foreign Application Priority Data

Jan. 31, 2013 (CN) .......................... 2013 1 0038054

(51) Int. Cl.
| | |
|---|---|
| *G01V 3/00* | (2006.01) |
| *A61B 6/03* | (2006.01) |
| *G01R 33/28* | (2006.01) |
| *A61B 6/04* | (2006.01) |
| *A61B 6/08* | (2006.01) |
| *A61B 6/00* | (2006.01) |
| *A61B 5/055* | (2006.01) |

(52) U.S. Cl.
CPC .............. *A61B 6/03* (2013.01); *A61B 6/0457* (2013.01); *A61B 6/08* (2013.01); *A61B 6/545* (2013.01); *A61B 6/589* (2013.01); *G01R 33/28* (2013.01); *A61B 5/0555* (2013.01); *A61B 2562/08* (2013.01)

(58) Field of Classification Search
USPC ........................................................ 324/309
See application file for complete search history.

(56) References Cited

U.S. PATENT DOCUMENTS 4,558,458 A * 12/1985 Katsumata ........... A61B 6/0457
378/20
5,072,121 A * 12/1991 Jazbec .................... G01T 1/166
250/221

(Continued)

*Primary Examiner* — Rodney Fuller

(57) ABSTRACT

An imaging system for achieving automatic detection of a patient's body profile and intelligent positioning of the patient. The imaging system includes at least one transmitter disposed on one side of a bore of the imaging system, and a receiver disposed on the other side of the bore of the imaging system. The at least one transmitter is configured to transmit a beam incapable of effectively penetrating a scan object. The receiver is configured to receive the beam transmitted by the at least one transmitter and to send a received signal to a processing device. The processing device is electrically connected to the receiver, and configured to determine whether the beam transmitted by the at least transmitter is blocked by the scan object according to the received signal so as to determine a position of the scan object.

18 Claims, 9 Drawing Sheets

(56) References Cited

U.S. PATENT DOCUMENTS

| | | | | |
|---|---|---|---|---|
| 6,385,430 | B1* | 5/2002 | Jackson | G01D 5/342 250/208.6 |
| 6,495,832 | B1* | 12/2002 | Kirby | G01V 8/20 250/222.2 |
| 7,857,513 | B2* | 12/2010 | Li | A61B 6/032 378/195 |
| 9,078,628 | B2* | 7/2015 | Cumpson | A61B 5/0555 |
| 2002/0079466 | A1* | 6/2002 | Talmi | G01D 5/347 250/559.1 |
| 2004/0082852 | A1* | 4/2004 | Cherek | A61B 6/0457 600/427 |
| 2005/0031082 | A1* | 2/2005 | Haaga | A61B 5/0064 378/108 |
| 2007/0238957 | A1* | 10/2007 | Yared | A61B 5/0059 600/407 |
| 2008/0021349 | A1* | 1/2008 | Sakai | A61B 5/1079 600/587 |
| 2009/0285357 | A1* | 11/2009 | Khamene | A61B 6/08 378/20 |
| 2010/0299014 | A1* | 11/2010 | Bouvier | A61B 6/4405 701/25 |
| 2013/0148778 | A1* | 6/2013 | Durgan | A61B 6/032 378/20 |
| 2014/0233041 | A1* | 8/2014 | Reitz | A61B 6/08 356/614 |
| 2015/0327831 | A1* | 11/2015 | Levin | A61B 6/545 600/427 |

* cited by examiner

AUTOMATIC DETECTION OF PATIENT BODY PROFILE AND INTELLIGENT POSITIONING OF PATIENT

CROSS REFERENCE TO RELATED APPLICATIONS

The present application is a continuation of and claims priority to U.S. patent application Ser. No. 14/167,591, filed Jan. 29, 2014, which claims priority to Chinese Patent Application No. 201310038054.2, filed on Jan. 31, 2013, the entire contents of which are incorporated herein by reference.

TECHNICAL FIELD

The present invention relates to an imaging system, and more particularly, to automatic detection of a patient body profile and intelligent positioning of a patient within an imaging system.

BACKGROUND ART

In such imaging systems as CT (Computed Tomography), prior to scanning, a center of an interested location of a patient, the location of interest needs to be aligned with a center of a CT gantry.

In the existing CT imaging system, the general positioning process is as follows: first let the patient lie on the scan bed, next, the doctor utilizes the pedal or the like to move the scan bed to a fixed height and position; then, the laser positioning lamp, which is adjacent to the X-ray tube is turned on, and a location of the patient's body irradiated by the laser positioning lamp is observed while finely tuning the position of the scan bed, such that the laser positioning lamp irradiates the scan reference location of the patient; next, the height of the scan bed is finely tuned taking into account the patient's height so as to move the center of the interested location of the patient into the center of the bore of the gantry; and finally, the positioning-setting button on the gantry is pressed to exhibit completion of the positioning.

Since patients differ from each other in body profile and interested locations, in the existing CT apparatus, the doctor, before the actual scan, needs to manually adjust the position and height of the scan support table several times through visual observation and by pressing the adjustment button so as to suit each patient. This makes the whole scanning process slow. Additionally, since there is no effective means for positioning the patient, patient positioning depends on the doctor's observation to determine whether the patient is positioned in an appropriate position, which depends on the doctor's experience and makes the positioning process inaccurate. Thus, inaccuracy in detection arises and the imaging quality is affected.

Therefore, a technology of quickly and accurately moving a patient to an appropriate position is required.

SUMMARY OF THE INVENTION

One object of the present invention is to solve at least one of the above identified problems and provide techniques of detecting a patient profile and automatically setting the height of a scan support table according to the patient profile, thereby positioning the patient more quickly and more accurately and improving the image quality.

Another object of the present invention is to provide a technique of quickly and accurately moving an interested location of a patient to a gantry in a direction in which the patient goes in and out a bore.

In an embodiment of the present invention, there is provided an imaging system, including: a scan support member for supporting a scan object, the scan support member being provided with a machine identifiable code representing a distance from a position of the machine identifiable code to one end of the scan support member; a processing means; and an identification means electrically connected to the processing means, the identification means identifying the machine identifiable code, decoding the distance represented by the machine identifiable code and sending the distance represented by the machine identifiable code to the processing means, wherein the processing means determines a distance from an interested location of the scan object to a scanning plane of the imaging system according to the distance represented by the machine identifiable code.

In another embodiment of the present invention, there is provided a method of positioning a scan object in an imaging system, including: identifying and decoding a machine identifiable code provided on a scan support member for supporting the scan object, the machine identifiable code representing a distance from a position of the machine identifiable code to one end of the scan support member; and determining a distance from an interested location of the scan object to a scanning plane of the imaging system according to the decoded distance represented by the machine identifiable code.

In another embodiment of the present invention, there is provided an imaging system, including: a transmitter disposed on one side of a bore of the imaging system, the transmitter transmitting a beam incapable of effectively penetrating a scan object; a receiver disposed on the other side of the bore of the imaging system, the receiver receiving the beam transmitted by the transmitter and sending a received signal to a processing means; and the processing means electrically connected to the receiver, the processing means judging whether the beam transmitted by the transmitter is blocked by the scan object according to the received signal so as to determine a position of the scan object.

In yet another embodiment of the present invention, there is provided a method of positioning a scan object in an imaging system, including: transmitting a beam incapable of effectively penetrating the scan object using a transmitter disposed on one side of a bore of the imaging system; receiving the beam transmitted by the transmitter and generating a received signal using a receiver disposed on the other side of the bore of the imaging system; and judging whether the beam transmitted by the transmitter is blocked by the scan object according to the received signal of the receiver so as to determine a position of the scan object.

With the imaging system and the method of positioning a scan object in an imaging system as mentioned above, the present invention can quickly and accurately move the interested location of the scan object to the scanning plane of the imaging system and align the center of the interested location of the scan object with the center of the scanning plane.

BRIEF DESCRIPTION OF THE DRAWINGS

When detailed descriptions of the embodiments of the present invention are read with reference to the accompanying drawings, features and advantages of the present invention will become better understood. In the drawings.

DETAILED DESCRIPTION

In the following detailed description, embodiments of the present invention are described with reference to the accompanying drawings. The CT (Computed Tomography) system described hereinafter is by way of example, and it shall be appreciated by persons skilled in the art that the principle of the present invention is also applicable to other imaging systems such as MRI (Magnetic Resonance Imaging) systems and PET (Positron Emission Tomography) systems. Furthermore, the patient described hereinafter as the scan object is by way of example, and it shall be appreciated by those skilled in the art that the principles of the present invention are also applicable to scan objects such as animals and plants, goods and the like.

The term "electrically connected" described in the present disclosure refers to a direct or indirect electrical connection between two devices. For example, description that a first device is electrically connected to a second device can mean that the first device is electrically connected directly to the second device, or that the first device is electrically connected to the second device by way of other devices. Similarly, in the present disclosure, sending data from a first device to a second device may refer to sending the data directly from the first device to the second device, or sending the data from the first device to the second device by way of other devices.

In the present disclosure, for convenience of description, the height direction of the CT system is defined as Y direction; the direction in which the patient goes into and out of the gantry is defined as Z direction; and the direction perpendicular to both the Y direction and the Z direction is defined as X direction.

Figure 1:
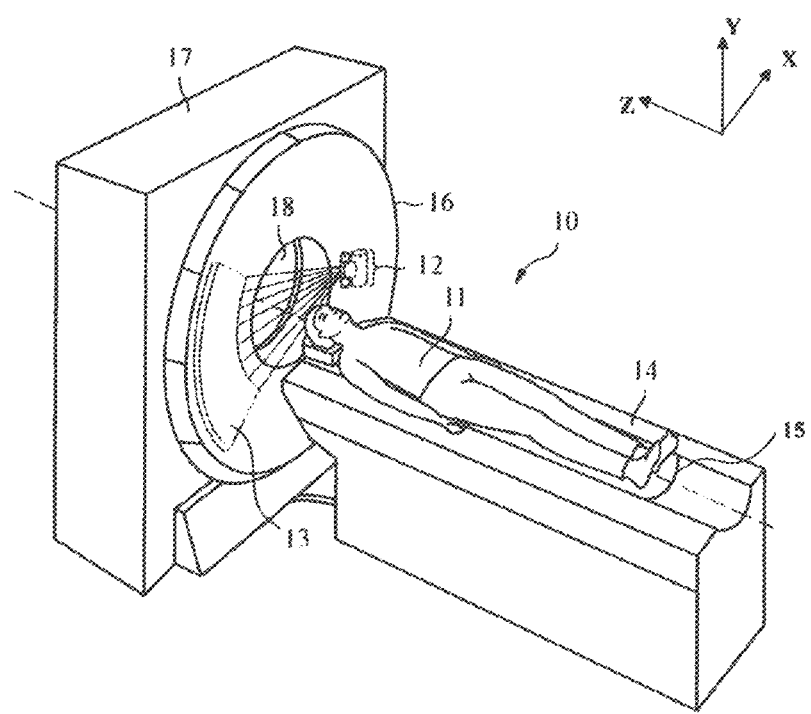
FIG. 1 is a schematic stereogram illustrating an embodiment of an imaging system of the present invention.

FIG. 1 is a schematic stereogram illustrating an embodiment of an imaging system 10 of the present invention. The imaging system 10 includes a scan support table 14, a gantry 17, and an Operating Console (OC, not shown). The scan support table 14 is used for supporting a patient 11, as a scan object, and can be shifted in the X, Y and Z directions through a scan support table shifting means not shown. The scan support table 14 includes a scan support cradle 15. The patient 11 lies on the scan support cradle 15, and through a scan support cradle shifting means not shown, the scan support cradle 15 can be shifted relative to the scan support table 14. The gantry 17 includes a rotating portion 16, and a bore 18 provided in a manner that the scan support cradle 15 and the patient 11 may go in and out. The rotating portion 16 is provided with an X-ray tube 12 for emitting X-rays and a detector 13 for receiving X-rays that penetrate the body of the patient 11. The X-ray tube 12 is provided with a collimating means for collimating the X-rays emitted by the X-ray tube 12. Hereinafter, the plane which the X-rays pass through is referred to as a scanning plane. Since attenuation of the X-rays when passing through an interested location of the patient 11 varies at different positions thereof, signals received by the detector 13 can reflect different X-ray adsorbing conditions for the interested location of the patient 11. The detected signals are sent by the detector 13 to a processing means (not shown) of the operating console so as to calculate and analyze information concerning the body of the patient 11. With rotation of the rotating portion 16, the interested location of the patient 11 is scanned from all angles.

Prior to the scan, the interested location of the patient needs to be shifted in the Z direction to the scanning plane in the gantry 17, and the center of the interested location of the patient 11 needs to be aligned with the center of the CT system's bore 18 (i.e. the center of the gantry 17) in the X and Y directions.

One embodiment of the present invention shows techniques of quickly and accurately positioning a scan object and moving the scan object accurately to the scanning plane within an imaging system.

Figure 2:
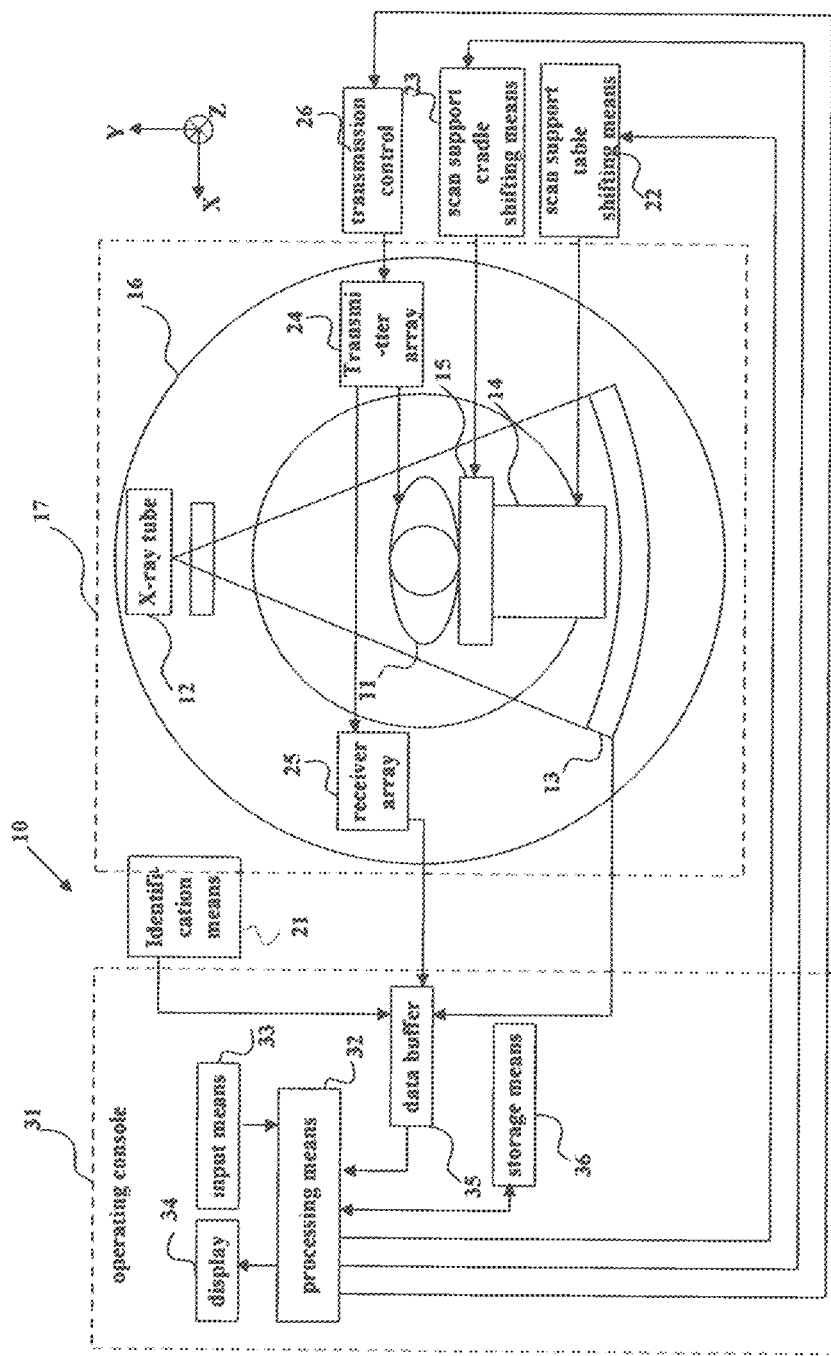
FIG. 2 is a block diagram illustrating an imaging system of an embodiment of the present invention.

FIG. 2 is a block diagram illustrating an imaging system 10 of an embodiment of the present invention. The imaging system 10 includes a scan support table 14, a gantry 17, an identification means 21, and an operation console 31.

The gantry 17 includes a rotating portion 16, and a bore 18 provided in a manner that a scan support cradle 15 and a patient 11 may go in and out. The rotating portion 16 of the gantry 17 is provided with an X-ray tube 12, a detector 13, a transmitter array 24 and a receiver array 25. The transmitter array 24 includes one or more transmitters located on one side of the bore 18 and configured to transmit beams that can not effectively penetrate the patient 11 as a scan object. The receiver array 25 includes one or more receivers located on the other side of the bore 18 and configured to receive the beams transmitted by the transmitter and send the resulting received signals to a processing means 32 of the operating console 31. The gantry 17 may further include a transmission control 26, which receives control signals from the processing means 32 of the operation console 31 to control whether the transmitter should transmit beams. Furthermore, the transmission control 26 can also be a button disposed on the gantry 17 or the scan support table 14. The button can be pressed by the doctor to control whether the transmitter is to transmit the beams. The transmission control 26 may not be provided, such that the processing means 32 is configured to directly control transmission of the transmitter array 24.

The so-called "beams that can not effectively penetrate the scan object" refer to beams that can not pass through the scan object, or beams that can not be effectively identified by the receiver after passing through the scan object. These include, but are not limited to: beams that are completely absorbed by the scan object; beams that can not be effectively received by the receiver due to extremely low beam intensity after passing through the scan object; beams that can not be effectively identified by the receiver due to the fact that the beams have passed through the scan object, resulting in such low intensity that the signals received by the receiver are extremely weak and thus immersed in the noise; and beams that are judged as effective signals are not received by the receiver due to the fact that the beams have passed through the scan object, resulting is such low intensity that the signals received by the receiver are lower than a certain threshold, and the like.

The scan support table 14 is provided with a scan support cradle 15, a scan support table shifting means 22, and a scan support cradle shifting means 23. The scan support table shifting means 22, under the control of the processing means 32, moves the scan support table 14 and the scan support cradle 15 thereon together in the X, Y and Z directions. The scan support cradle shifting means 23, under the control of the processing means 32, moves the scan support cradle 15 relative to the scan support table 14.

The operating console 31 includes the processing means 32, an input means 33, a display 34, a data buffer 35, and a storage means 36. The data buffer 35 receives data from the identification means 21, the receiver array 25 and the detector 13. The processing means 32 reads, calculates and analyzes the data in the data buffer 35, and according to the data from the identification means 21, the receiver array 25 and/or the input means 33, controls operations of the scan support table shifting means 22, the scan support cradle shifting means 23, the transmission control 26 and the like. The processing means 32 may not be disposed within the operating console 31, but can be disposed on the gantry 17 and other parts of the imaging system 10. The storage means 36 for storing data and instructions can be, for example, RAM, ROM, a hard disk or the like. The processing means 32 can read the data and instructions in the storage means 36, and can also write the data and instructions into the storage means 36. The display 34 displays data output by the processing means 32, for example, an image of the interested location of the patient 11, an operation interface to be controlled by a user, or the like. The user can input data and/or instructions via the input means 33 to control operation of the imaging system 10 or a part thereof. The display 34 may also have an input function, so that the input means 33 can be omitted. For example, the display 34 may be a touch screen display though which the user inputs commands.

Figure 3A:
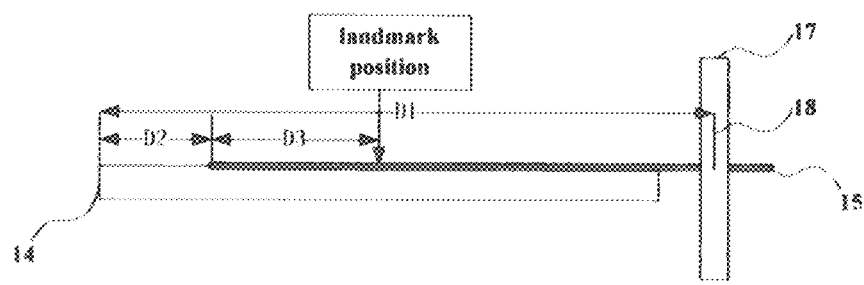
FIG. 3A is a schematic diagram illustrating a principle of positioning a patient in the Z direction according to an embodiment of the present invention.

FIG. 3A is a schematic diagram illustrating a principle of positioning a patient in the Z direction according to an embodiment of the present invention. As shown in FIG. 3A, the scan support cradle 15 is provided with a machine identifiable code like OID (Optical Identity) stealth codes, for example, OID stealth codes can be imprinted on the scan support cradle 15, or a tag with OID stealth codes can be affixed to the scan support cradle 15. Each OID stealth code represents a distance from a position of the OID stealth code to an end of the scan support cradle 15, and can be identified by the identification means 21 in FIG. 2. The identification means 21, which is electrically connected to a processing means 32 of an operating console 31, can identify the machine identifiable code, decode the distance represented by the machine identifiable code and send the distance represented by the machine identifiable code to the processing means 32. The identification means 21 may be, for example, a reader pen as shown in FIG. 4.

Figure 3B:
FIG. 3B is a schematic diagram illustrating scales with OID stealth codes according to an embodiment of the present invention.

FIG. 3B is a schematic diagram illustrating scales with OID stealth codes according to the present invention. The scale imprinted on the scan support cradle 15 can be a length unit, or a picture. For example, the scan support cradle 15 can be formed into a pattern with scales as shown in FIG. 3B, into which the OID stealth codes are placed. The OID codes may be marked with 1 mm units.

Figure 4:
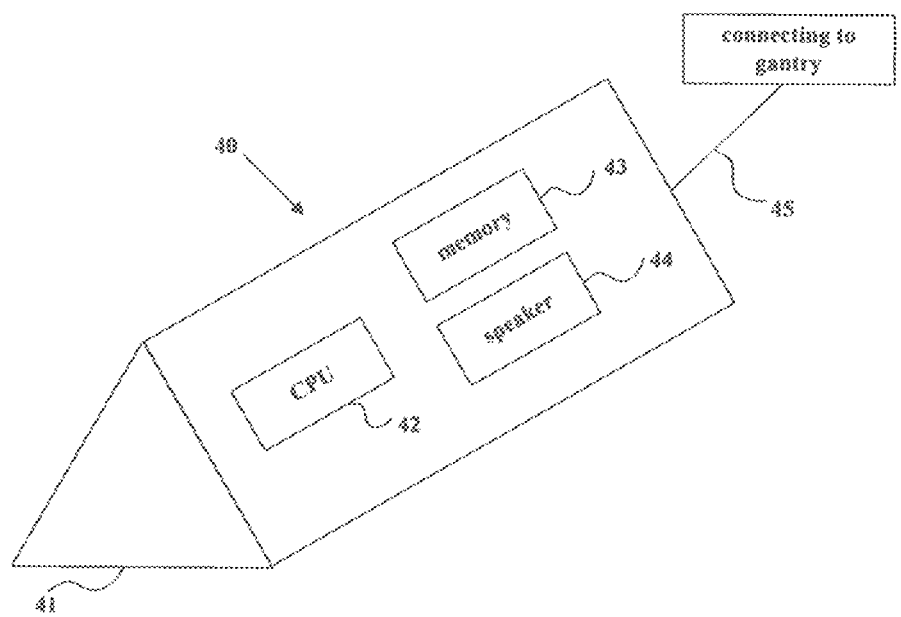
FIG. 4 is a block diagram illustrating a reader pen according to an embodiment of the present invention.

FIG. 4 is a block diagram illustrating a reader pen 40. As shown in FIG. 4, the reader pen 40 includes: a reading head 41 for reading OID stealth codes; CPU 42; a memory 43; a speaker 44 for prompting the user; and a connecting wire 45 for connecting to the gantry, which provides power to the reader pen 40, and also transfers data and commands to the gantry and then to the operating console 31 through the gantry. Said reader pen 40 is an example of the identification means 21. According to types of identification codes, other forms of identification means can also be used.

During operation, the user, with the reader pen 40 in a hand, presses the reading head 41 at the tip of the reader pen 40 on the OID stealth code. The reading head 41 identifies the OID stealth code, and sends the identified code (for example, binary data) to the CPU 42. The CPU 42 receives the code identified by the reading head 41, and according to a predetermined coding rule stored in the memory 43, decodes the identified code, thereby obtaining the distance represented by the OID stealth code on the scan support cradle 15. The speaker 44 makes a "beep" sound to prompt the user that the identification is successful, and sends the distance represented by the OID stealth code to the processing means 32 of the operating console 31, while being allowed to concurrently transmit a positioning command to the processing means 32 so as to request the processing means 32 to initiate a positioning process.

Referring back to FIG. 3A, the positioning principle of the present embodiment is detailed as follows.

When the imaging system 10 has been assembled, the scan support cradle 15 is moved to the original position. Subsequently, the distance (D1-D2) between the start of the scan support cradle 15, i.e., the first scale code of the OID stealth codes, and the scanning plane of the gantry 17 is stored in a storage means 36 of the operating console 31. Or, the distance D1 from the start of the scan support table 14 to the scanning plane of the gantry 17 and the distance D2 from the start of the scan support table 14 to the start of the scan support cradle 15 can be measured, preset as parameters through an input means 33 and stored in the storage means 36. Certainly, in the positioning process, the distance D1 from the start of the scan support table 14 to the scanning plane of the gantry 17 and the distance D2 from the start of the scan support table 14 to the head of the scan support cradle 15 can also be obtained in other manners.

If desiring to perform a CT scan of a certain location of the patient (i.e., an interested location, for example, a location near to the nose of the patient), the doctor only needs to use the OID stealth code reader pen 40 to read the OID code at the position corresponding to the interested location on the scan support cradle 15. The reader pen 40 identifies the OID code, decodes it into position information D3 which represents a distance from the position of the OID code to an end (for example, a left end in FIG. 3A) of the scan support cradle 15, and sends it to the processing means 32 of the operating console 31, where the processing means 32 determines a distance from the interested location (i.e., landmark position) of the patient 11 to the scanning plane of the imaging system 10. In addition, the processing means 32 controls the scan support cradle shifting means 23 to shift with a corresponding distance the scan support cradle 15 according to the determined distance from the interested location (i.e., the landmark position) of the patient 11 to the scanning plane of the imaging system 10, thereby shifting the interested location of the patient to the scanning plane in the bore 18 of the gantry 17.

The shifting distance is calculated in a manner as follows.

The distance D1 from the start (the left end) of the scan support table 14 to the scanning plane of the gantry 17 and the distance D2 from the start (the left end) of the scan support table 14 to the start (the left end) of the scan support cradle 15 are known in advance. Besides, the distance D3 from the interested location (corresponding to the landmark position in FIG. 3A) to the start (the left end) of the scan support cradle 15 is obtained by decoding the OID stealth code. Therefore, the processing means 32 may calculate the distance from the landmark point to the scanning plane as D1-D2-D3. Since the reading position of the reader pen 40 is the reference point (the landmark position) of the scan, accurate positioning of the patient 11 can be achieved. Furthermore, the scan support cradle shifting means 23 can move the scan support cradle 15 with the distance of D1-D2-D3 as calculated by the processing means 32, thereby accurately moving the interested location of the patient 11 to the scanning plane of the gantry 17.

The reader pen 40 can be used to simply read the OID stealth code. Moreover, the tip of the reader pen 40 is relatively small, thereby promoting positioning accuracy. Thus, in the above embodiment, the OID stealth codes are adopted to place on the scales (distance information). However, such optical identifiable codes as two-dimensional codes and bar codes, or other machine identifiable codes can also be adopted to place on the scales. In this case, other code identification means corresponding to the adopted machine identifiable codes needs to be employed.

In addition to positioning the OID stealth codes at one side of the scan support cradle 15, in an embodiment, the OID stealth codes are positioned throughout the scan support cradle 15 in a width direction, or arrange the OID stealth codes on both sides of the scan support cradle 15 so as to facilitate the doctor to do a positioning conveniently on both sides of the scan support table 14.

In the embodiment as shown in FIG. 3A, OID stealth codes are imprinted on the scan support cradle 15. Each OID stealth code represents a distance from the position thereof to the left end of the scan support cradle 15. In calculating the distance from the interested location of the patient 11 to the scanning plane of the imaging system 10, the distance from the interested location (corresponding to the read OID stealth code) of the patient 11 to the scanning plane is calculated by subtracting the distance D2 from the left end of the scan support table 14 to the left end of the scan support cradle 15 and the distance D3 (i.e., the distance represented by the OID stealth code) from the left end of the scan support cradle 15 to the landmark position from the distance D1 from the left end of the scan support table 14 to the scanning plane. However, the present invention is not limited thereto. According to another embodiment of the present invention (see FIG. 5), the OID stealth codes can also be imprinted on the scan support table 14; and the distance from the interested location of the patient 11 to the scanning plane can be determined in other manners.

Figure 5A:
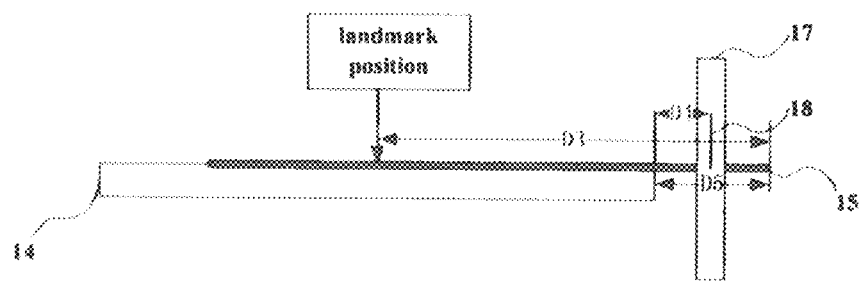
FIGS. 5A, 5B, and 5C are diagrams illustrating principles of positioning a patient in the Z direction according to other embodiments of the present invention.
Figure 5B:
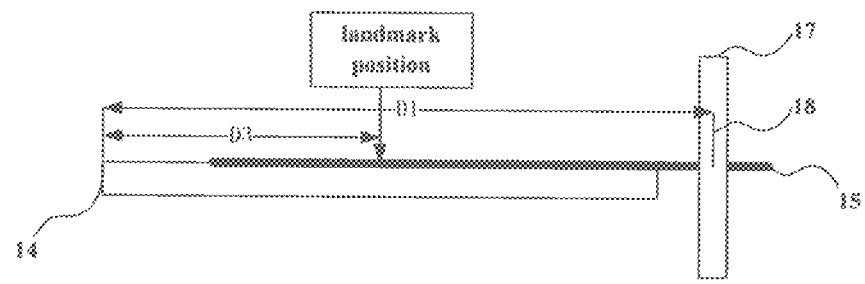
Figure 5C:
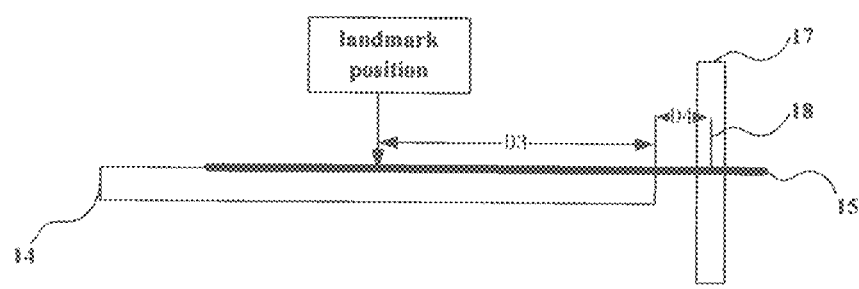

FIGS. 5A, 5B, and 5C are diagrams illustrating principles of positioning a patient in the Z direction according to other embodiments of the present invention.

In an embodiment, as shown in FIG. 5A, an OID stealth code represents a distance from the position thereof to the right end of a scan support cradle 15, i.e., the marking of OID stealth code begins from the end portion of the scan support cradle 15. In this case, a distance from an interested location of the patient 11 to the scanning plane, can be calculated by using a distance D4 from the right end of a scan support table 14 to the scanning plane, a distance D5 from the right end of the scan support table 14 to the right end of the scan support cradle 15 and a distance D3 from the right end of the scan support cradle 15 to the landmark position (i.e., the distance represented by the OID stealth code), i.e., D3-(D5-D4). Further, the lengths of the scan support table 14 and the scan support cradle 15 are already known. D4 and D5 can be calculated through a simple linear relation of D1 and D2 in FIG. 3A. Stated in another way, the distance from the interested location of the patient 11 to the scanning plane can also be calculated by way of D1, D2, D3, and the lengths of the scan support table 14 and the scan support cradle 15.

In an embodiment as shown in FIG. 5B, OID stealth codes are imprinted on a scan support table 14. Each OID stealth code represents a distance from the position thereof to the left end of the scan support table 14. In calculating a distance from an interested location of the patient 11 to the scanning plane of the imaging system 10, the distance from the interested location of the patient 11 to the scanning plane is calculated by subtracting the distance D3 (i.e., the distance represented by the OID stealth code) from the left end of the scan support table 14 to the landmark position from the distance D1 from the left end of the scan support table 14 to the scanning plane.

In an embodiment, as shown in FIG. 5C, OID stealth codes are imprinted on a scan support table 14. Each OID stealth code represents a distance from the position thereof to the right end of the scan support table 14. In calculating a distance from an interested location of the patient 11 to the scanning plane of the imaging system 10, the distance from the interested location of the patient 11 to the scanning plane is calculated by adding the distance D3 (i.e., the distance represented by the OID stealth code) from the right end of the scan support table 14 to the landmark position to the distance D1 from the right end of the scan support table 14 to the scanning plane.

After the distance from the interested location of the patient 11 to the scanning plane is obtained, the scan support table 14 and/or the scan support cradle 15 can be shifted in the Z direction through a scan support table shifting means 22 and/or a scan support cradle shifting means 23, such that the scan support table 14 and the scan support cradle 15 have been moved said distance.

FIG. 3A and FIGS. 5A, 5B, and 5C illustrate embodiments of the present invention where the scan support cradle 15 or the scan support table 14 is provided with a machine identifiable code. Nonetheless, the present invention is not limited thereto. In other embodiments, it is also applicable to more generally provide a scan support member for supporting a scan object with a machine identifiable code representing a position of the machine identifiable code to an end of the scan support member. Moreover, it is also applicable to more generally arrange a scan support member shifting means to move the scan support member according to a distance from an interested location of the scan object to the scanning plane determined by a processing means.

Figure 6:
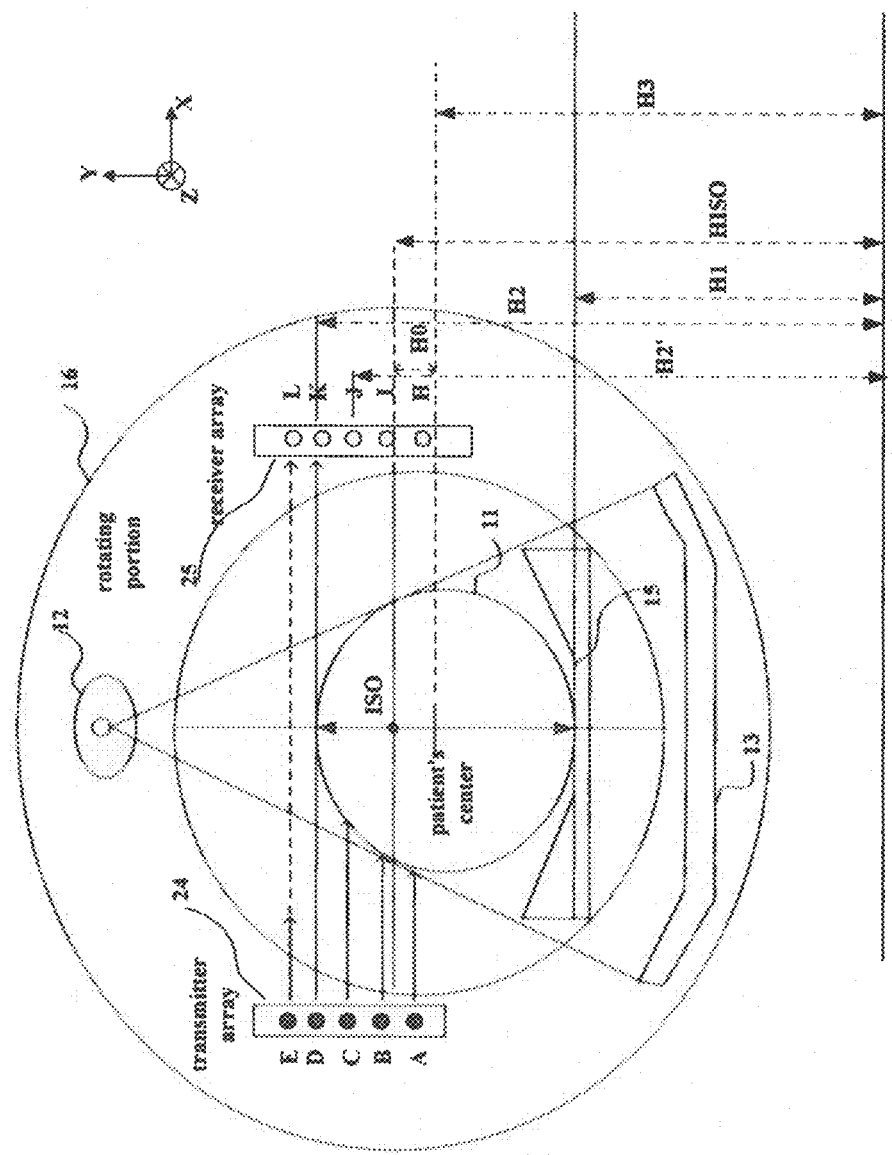
FIG. 6 is a schematic diagram illustrating a principle of positioning a patient in Y direction according to an embodiment of the present invention.
Figure 7:
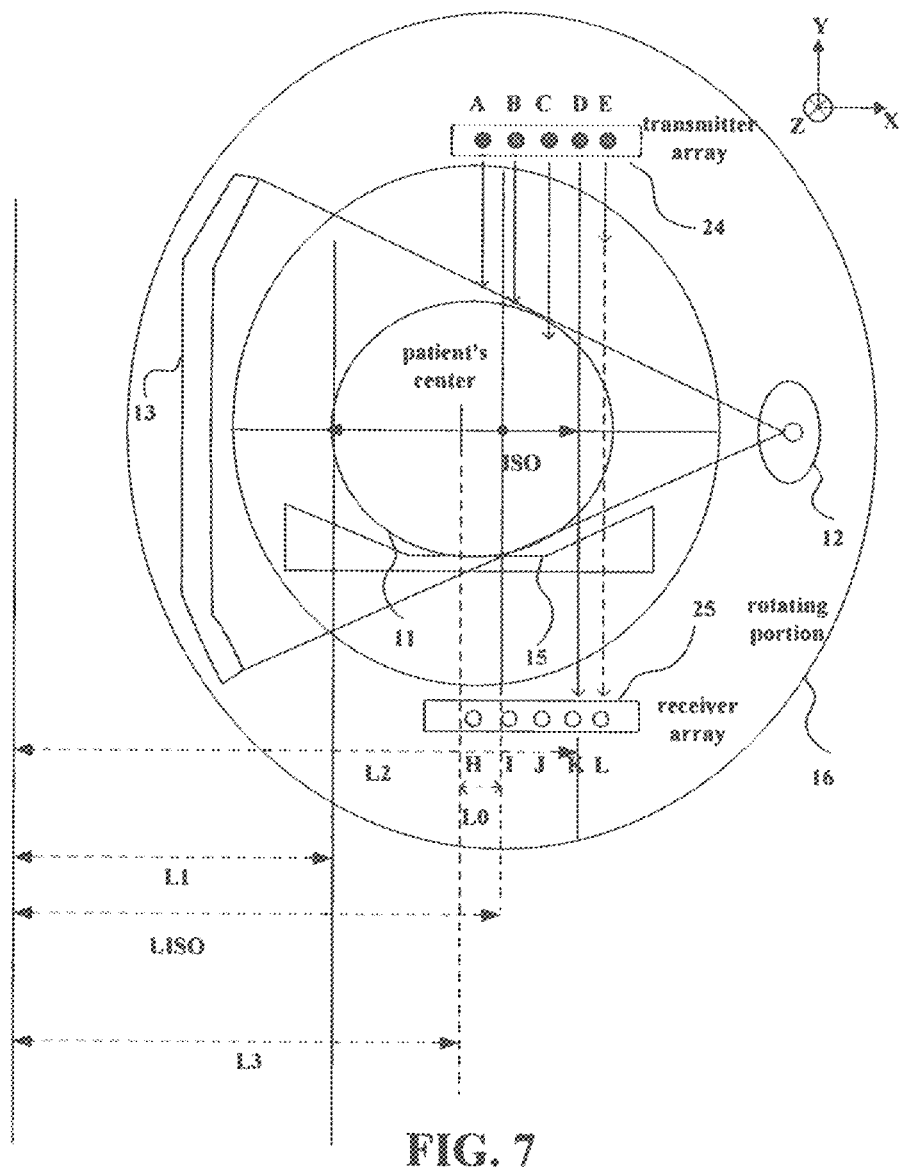
FIG. 7 is a schematic diagram illustrating a principle of positioning a patient in X direction according to an embodiment of the present invention.
Figure 8:
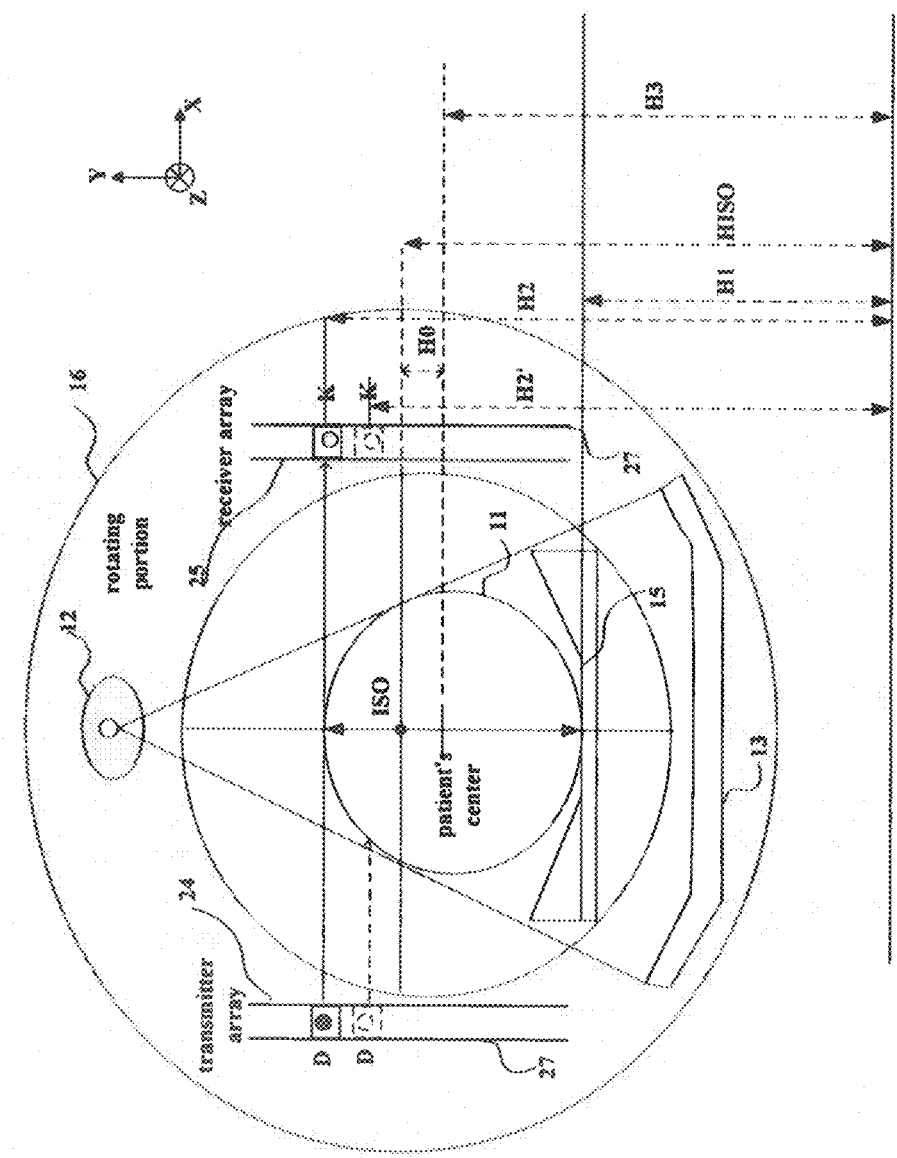
FIG. 8 is a schematic diagram illustrating a principle of positioning a patient in Y direction according to another embodiment of the present invention.

FIG. 6 is a schematic diagram illustrating a principle of positioning a patient in the Y direction according to an embodiment of the present invention. In a patient positioning apparatus as shown in FIG. 6, a transmitter array 24 is disposed at a left side of a rotating portion 16 of a gantry 17; and a receiver array 25 is correspondingly disposed at a right side thereof. The transmitter array 24 and the receiver array 25 can rotate with rotation of the rotating portion 16, or can be mounted at a stationary portion of the gantry. The transmitter array 24 emits beams that can not effectively penetrate the scan object. In the embodiment shown, the transmitter array 24 includes five optical transmitters A-E which emit visible light, and the receiver array 25 includes five optical receivers H-L. The present invention does not limit the numbers of transmitters and receivers included in the transmitter array 24 and the receiver array 25, respectively. In the embodiment shown in FIG. 6, the number is "more than 2". In an embodiment, optical receivers H-L are photo sensors. Positions of the transmitter array 24 and the receiver array 25 are not limited to the respective left and right sides of the gantry 17, as long as enabling beams are transmitted by each optical transmitter A-E in the transmitter array 24 to reach the respective optical receivers H-L in the receiver array 25 along the X direction (as shown in FIGS. 6 and 8) or the Y direction (as shown in FIG. 7) by means of the rotation of the rotating portion 16.

As shown in FIG. 6, a portion of light transmitted by the transmitter array 24 is blocked by a patient 11 or a part of the body thereof, so that the portion of light can not reach the respective receiver array 25. In FIG. 6, light transmitted by the optical transmitters D and E can reach the optical receivers K and L such that the optical receivers K and L can detect the light. By contrast, light transmitted by the optical transmitters A, B and C can not reach the receiver array 25 such that the optical receivers H, I and J can not detect the light. Signals output from the optical receivers K and L are, for example, high levels. Signals output from the optical receivers H, I and J are, for example, low levels. The receiver array 25 transmits the resulting received signals to a processing means 32. The processing means 32 judges whether beams (light in this embodiment) transmitted by the transmitters A-E are blocked by the scan object according to the received signals, thereby determining the position of the scan object. This data processing can be implemented using the processing means 32 located on an operating console, or a data processing means located on the gantry.

In FIG. 6, a minimum height of the receivers (K and L as shown in FIG. 6), which receive light, is defined as H2. Height of the scan support cradle 15 is defined as H1. Height of the center ISO (scan rotation center) of a bore 18 is defined as HISO. Height of the center of the interested location of the patient 11 is defined as H3. The distance from the center of the interested location of the patient 11 to the center ISO of the bore 18 is defined as H0. It needs to move the scan support table 14 and the scan support cradle 15 to eliminate H0, such that the center of the interested location of the patient 11 coincides with the center of the bore 18. H1 and HISO can be measured in advance, preset as parameters through an input means 33, and stored in a storage means 36. Certainly, in the positioning process, H1 and HISO can also be obtained in other manners.

In FIG. 6, the center H3 of the interested location of the patient 11 and the distance H0 with which the patient 11 needs to be moved are calculated in manners as follows:

$$H3 = H1 + \frac{1}{2} \times (H2 - H1) = \frac{1}{2} \times (H2 + H1).$$

$$H0 = HISO - H3.$$

In view of the foregoing, through the optical transmitters and optical receivers pairs positioned on both sides of the bore of the imaging system, the processing means 32 can determine the Y-direction position of the patient's body, and move the scan support table 14 to adjust the patient's height. The scan support table 14 can be moved through a scan support table shifting means 22 according to the distance determined by the processing means 32, thereby adjusting the height H1 of the patient 11 until H0 is equal to 0. That is, the center of the interested location of the patient 11 is aligned with the center of the bore 18 (the center of the gantry 17).

In FIG. 6, the height H2 of the optical transmitter D is selected as a positioning reference of the upper edge of the patient 11. The beam of light transmitted by the optical transmitter D is not blocked by the patient 11; and light transmitted by the optical transmitter C adjacent to D is blocked by the patient 11. Similarly, the height H2' of the optical transmitter C can also be selected as a positioning reference. The beam of light transmitted by the optical transmitter C is blocked by the patient 11; and light transmitted by the optical transmitter D adjacent to C is not blocked by the patient 11.

As shown in FIG. 6, the height H2 of the optical transmitter D is higher than the upper edge of the patient 11, and the height H2' of the optical transmitter C is lower than the upper edge of the patient 11. The error calculated in this way is the distance between the optical transmitter C and the optical transmitter D, i.e., H2−H2'. In order to further reduce the error, the average height (H2+H2')/2 of the optical transmitters C and D are, in an embodiment, used to replace H2. Therein, light transmitted by the optical transmitter C is blocked by the patient 11; and light transmitted by the optical transmitter D adjacent to C is not blocked by the patient 11. The average error calculated in this way is half the distance between the optical transmitter C and the optical transmitter D, i.e., (H2−H2')/2.

Similarly, in order to improve accuracy of calculation, in an embodiment of the present invention, a distance between each sensor is, in an embodiment, 3-5 mm or less. However, if a distance between the optical transmitters is too small, interference between the optical transmitters increases, which may not be conducive to accurate positioning of the patient.

Other beams (i.e., other than light), such as electromagnetic waves or acoustic waves, may also be used, but need to satisfy the following conditions: (1) being harmless to the human body; (2) being incapable of effectively penetrating the human body; (3) having a small divergence angle so that width of the beams is maintained in a magnitude of a millimeter after the beams are radiated to tens of centimeters; and (4) being capable of being easily converted mutually to electrical signals and involving miniaturized transmitters and receives. In an embodiment of the present invention, a laser light source with a relatively small divergence angle, for example, He—Ne laser, can be used to improve the positioning accuracy. In an embodiment of the present invention, a collimating means may be used for collimating the laser. In another embodiment, light-emitting diode (LED), laser diode (LD), a semiconductor laser and the like are, in an embodiment, used as transmitters so as to save costs.

In another embodiment of the present invention, non-visible light (e.g., near-infrared light), ultrasonic waves and the like are, in an embodiment, used to replace He-Ne laser in order to avoid impact on the patient's vision.

It should be noted that, the patient positioning principle in this embodiment is not the same as a conventional laser positioning lamp. The conventional laser positioning lamp emits laser light in the Y direction. The doctor moves the patient in the Z direction according to positions of light spots resulting from the laser positioning lamp irradiating the body of the patient 11. However, the laser positioning lamp needs to rely on subjective judgment of the doctor to determine the position of the patient 11, so the position of the patient can not be accurately determined; moreover, visible light facilitating the doctor's observation needs to be emitted.

After the interested location of the patient 11 is placed in the center of the bore 18, a process of positioning the patient in the Y direction is carried out. The transmitter array 24 is started only by pressing a button or through an input means 33 (for the sake of safety). Then, the system can automatically initiate a scan support table shifting means 22 to shift the scan support table 14 until the center of the interested location of the patient coincides with the center of the gantry.

By using the Y direction positioning process of the present embodiment, the patient's body profile can be accurately positioned, and the height of the scan support table can be automatically set according to the patient's body profile, thereby more accurately aligning the actual center of the patient with the ISO center. In this way, the patient can be more quickly and accurately positioned, thereby improving the image quality and accelerating the whole scanning process.

In the above embodiment, the center of the patient 11 in the Y direction is calculated by detecting the upper edge of the interested location of the patient 11 and using the height of the lower edge of the interested location of the patient 11 (i.e., the height of the scan support cradle 15). Similarly, the rotating portion 16 can also be rotated by 90 degrees, so that the patient is positioned in the X direction. When the rotating portion 16 is rotated by 90 degrees, the center of the patient 11 in the X direction can be calculated by detecting the left edge of the interested location of the patient 11 and the right edge of the interested location of the patient 11; and the scan support table 14 is moved in the X direction to align the X-direction center of the patient with the ISO of the gantry 17.

FIG. 7 shows this case. FIG. 7 is a schematic diagram illustrating a principle of positioning a patient in the X direction according to an embodiment of the present invention. The rotational portion 16 in FIG. 6 is rotated by 90 degrees to determine an X-direction position of the body of the patient 11. Similar to FIG. 6, a position L2 of the right edge of the interested location of the patient 11 is detected first. As shown in FIG. 7, a portion of light transmitted by a transmitter array 24 is blocked by the patient 11 or a part of the body thereof, so that the portion of light can not reach a respective receiver array 25. In FIG. 7, light transmitted by optical transmitters D and E can reach optical receivers K and L such that the optical receivers K and L can detect the light. By contrast, light transmitted by optical transmitters A, B and C can not reach the receiver array 25 such that optical receivers H, I and J can not detect the light. The signal output levels from the optical receivers K and L are, for example, high. The signal output levels from the optical receivers H, I and J are, for example, low. The receiver array 25 sends the received signals to a processing means 32 for calculation. The processing means 32 judges whether the light transmitted by the transmitters A-E is blocked by the patient 11 according to the received signals, thereby determining the position of the right edge of the patient 11.

Similarly, in FIG. 7, the optical transmitter D can be selected as a positioning reference to determine the distance L2 from the right edge of the body of the patient 11 to a certain predetermined plane. The beam of light transmitted by the optical transmitter D is not blocked by the patient 11; and light transmitted by the optical transmitter C adjacent to D is blocked by the patient 11. Similarly, the position of the optical transmitter C can also be selected as a positioning reference to determine L2. The beam of light transmitted by the optical transmitter C is blocked by the patient 11; and light transmitted by the optical transmitter D adjacent to C is not blocked by the patient 11. In addition, the positions of the optical transmitters C and D can also be averaged to determine L2.

Then, L1 is similarly detected. The rotating portion 16 can be further rotated by 180 degrees to determine, by means of a similar method, the distance L1 from the left edge of the body of the patient 11 to said predetermined plane.

Then, the center of the patient 11 and the distance with which the patient 11 needs to be moved are calculated in manners as follows:

$$L3=\tfrac{1}{2}\times(L2+L1).$$

$$L=LISO-L3.$$

L1 and LISO can be measured in advance, preset as parameters through an input means 33, and stored in a storage means 36. Certainly, in the positioning process, L1 and LISO can be obtained in other manners.

Referring now to FIG. 8, FIG. 8 is a schematic diagram illustrating a principle of positioning a patient in the Y direction according to another embodiment of the present invention. In the embodiment of FIG. 8, the rotating portion 16 is further provided with a guide member 27. Transmitters in a transmitter array 24 and receivers in a receiver array 25 can move in a direction perpendicular to a direction where beams are transmitted. The transmitters and receivers can be moved in a continuous manner or in a stepwise manner. At this time, even if only a single optical transmitter D and a single optical receiver K are used, positioning of a patient 11 can also be easily and quickly achieved. As shown in FIG. 8, light transmitted by the optical transmitter D (shown with a solid line in FIG. 8) can reach the optical receiver K (shown with a solid line in FIG. 8). At this time, the height of the optical transmitter D is H2. The optical transmitter D and the optical receiver K move in a stepwise manner, and at a next moment, reach the positions as shown with a dotted line in FIG. 8, respectively. At this time, light transmitted by the optical transmitter D can not reach the optical receiver K; and the height of the optical transmitter D is H2'. A center H3 of the interested location of the patient 11 and a distance H0 with which the patient 11 needs to be moved are calculated in manners as follows:

$$H3=H1+\tfrac{1}{2}\times(H2-H1)=\tfrac{1}{2}\times(H2+H1).$$

$$H0=HISO-H3.$$

Also, H2' or (H2+H2')/2 can be used in place of H2 in the above equation.

In other words, the location of the scan object is determined according to one or both of, the location (for example, the solid-line position in FIG. 8) of the transmitter D at which the transmitted beam is not blocked by the scan object and a next or the preceding location (for example, the dotted-line position in FIG. 8) of the transmitter D at which the transmitted beam is blocked by the scan object.

Figure 9:
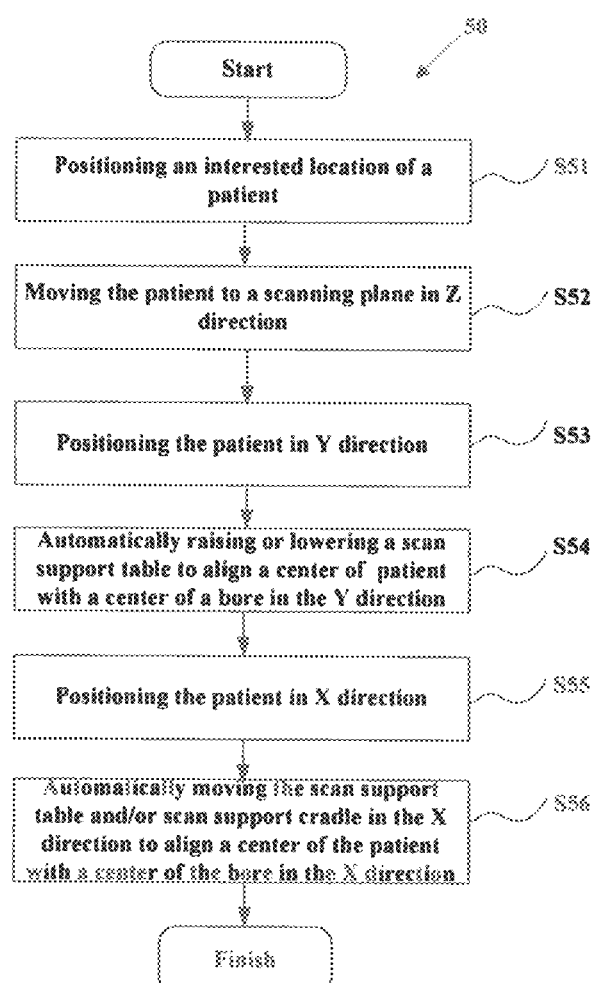
FIG. 9 is a flow chart illustrating a method of adjusting a position of a patient according to an embodiment of the present invention.

FIG. 9 is a flow chart illustrating a method 50 of adjusting a position of a patient according to the present invention. As shown in FIG. 9, in step S51, an interested location of the patient is positioned. In an embodiment, a patient 11 lies on a scan support cradle 15 of a scan support table 14, a doctor uses a reader pen 40 to read such machine identifiable codes as OID stealth codes imprinted on the scan support cradle 15 to select an interested location of the patient. A reading head 41 of the reader pen 40 identifies the selected OID stealth code; and the doctor is informed by a "beep" sound made by a speaker 44 included by the reading 40, or in another manner, that a landmark position has been successfully selected. The CPU 42 of the reader pen 40 decodes the OID stealth code to obtain a distance represented by the OID stealth code, and sends the distance represented by the OID stealth code to a gantry 17 and further to a processing means 32 by way of the gantry 17. Through the manner detailed above, the processing means 32 determines a distance from the interested location of the scan object to a scanning plane of an imaging system 10 according to the decoded distance represented by the machine identifiable code.

In a next step S52, according to the distance from the interested location of the scan object to the scanning plane of the imaging system 10, determined by the processing means 32, the processing means 32 controls a scan support table shifting means 22 and/or a scan support cradle shifting means 23 to move a scan support table 14 and/or a scan support cradle 15, so that the patient 11 is moved in the Z direction to the scanning plane.

In a next step S53, the patient 11 is positioned in the Y direction. After the patient is moved in the Z direction to the scanning plane, the identification and positioning of the patient's body profile can be initiated automatically or manually by the doctor (for example, by inputting a command through an input means 33 or pressing a button) in the Y direction. A transmitter disposed on one side of a bore 18 of the imaging system 10 is used to transmit beams (for example, light) incapable of effectively penetrating the patient 11, in which at least a portion of the transmitted light is blocked by the patient, and thus, can not reach the receiver. A receiver disposed on the other side of the bore 18 of the imaging system 10 is used to receive the beams transmitted by the transmitters and send the resulting received signal to the processing means 32. The processing means 32, through the manner detailed above, judges whether the beams transmitted by the transmitter are blocked by the patient 11 according to the received signal of the receiver, thereby determining a Y-direction position of the patient 11. The processing means 32 further determines a distance from a center of the interested location of the patient 11 in the Y direction to a center of the bore 18.

In a next step S54, the scan support table 14 is automatically raised or lowered to align the center of the patient 11 to the center of the bore 18 (ISO) in the Y direction. The processing means 32 controls the scan support table shifting means 22 to move the scan support table 14 in the Y direction, so that the center of the patient 11 is aligned with the center of the bore 18 in the Y direction.

In a next step S55, the patient 11 is positioned in the X direction. After the center of the patient 11 is aligned with the center of the bore 18 in the Y direction, identification and positioning of the patient's body profile can be initiated automatically or manually by the doctor (for example, by inputting a command through an input means 33 or pressing a button) in the X direction. A rotating portion is rotated by 90 degrees. A transmitter disposed on one side of a bore 18 of the imaging system 10 is used to transmit beams (for example, light) incapable of effectively penetrating the patient 11, in which at least a portion of the transmitted light is blocked by the patient, and thus, can not reach the receiver. A receiver positioned on the other side of the bore 18 of the imaging system 10 is used to receive the beams transmitted by the transmitter and transmit the resulting received signal to the processing means 32. The processing means 32, through the manner detailed above, judges whether the beams transmitted by the transmitter are blocked by the patient 11 according to the received signal of the receiver, thereby determining an X-direction position of the patient 11. The processing means 32 further determines a distance from a center of the interested location of the patient 11 in the X direction to a center of the bore 18.

In a next step S54, the scan support table 14 and/or the scan support cradle 15 are moved automatically in the X direction to align the center of the patient 11 with the center of the bore 18 in the X direction. The processing means 32 controls the scan support table shifting means 22 and/or the scan support cradle shifting means 23 to move the scan support table 14 and/or the scan support cradle 15 in the X direction, so that the center of the patient 11 is aligned with the center of the bore 18 in the X direction.

Through the above procedures, the interested location of the scan object can be quickly and accurately shifted to the scanning plane of the imaging system, and the center of the interested location of the scan object can be aligned with the center of the scanning plane.

In some embodiments of the present invention, one or more method steps can be omitted and/or implemented in a sequence different from the listed sequence. For example, in some embodiments of the present invention, some steps may not be implemented. In some embodiments of the present invention, patient positioning can be carried out first in the X direction, and then in the Y direction. As another example, some steps can be implemented in accordance with a time sequence different from that listed above (including simultaneously).

The processing means 32 of the present invention includes a processor (not shown) coupled to an interconnected bus. The processor may be any suitable processor, processing unit or microprocessor. In spite of not being shown in FIG. 2, the processing means 32 may be a multi-processor system and can include one or more additional processors coupled to the interconnected bus in communication.

One or more means (for example, the processing means 32) included in the operating console of the present invention can be located in a "cloud" side, and through the network, can be connected to other parts of the operations console 31. Such network connection includes, but is not limited to, wired and/or wireless connections made through LAN, WAN, MAN, Internet, hospital Intranet and the like.

The storage means 36 may include any type of volatile and/or nonvolatile memory, for example, static random access memory (SRAM), dynamic random access memory (DRAM), flash memory, read only memory (ROM), mass memory and the like. The mass memory can contain hard disk drive, optical drive, magnetic tape storage means and the like.

In some embodiments, any machine-readable medium method, system and computer program product are expected to achieve the above functionality. For example, in some embodiments, existing computer processors, or dedicated computer processors incorporated thereto for this or another purpose, or hard wire and/or firmware systems may be used to achieve the above functionality.

For example, one or more of the components of the above system and/or the method steps can be realized by hardware, firmware and/or a set of instructions of software alone or in combination. Some embodiments may be provided as a set of instructions residing on a computer readable medium (e.g., memory, hard disk, DVD or CD) for implementation of a general-purpose computer or other processing means.

This written description uses examples to disclose the invention, including the best mode, and also enables any skilled person in the art to practice the invention, including making and using any means or system and performing any incorporated method. The patentable scope of the invention is defined by the claims, and may include other examples that occur to those skilled in the art. Such other examples are intended to be within the range of the claims, if such other examples have structural elements that do not differ from the literal language of the claims, or if they include equivalent structural elements with insubstantial differences from the literal language of the claims.

What is claimed is:

1. An imaging system, comprising:
a scan support member shifting apparatus configured to shift the scan support member in at least one axis with respect to a bore of the imaging system, the shifting apparatus comprising:
an a hand-held identification device configured to:
identify a machine identifiable code on the scan support member, the machine identifiable code representing a distance from a position of the machine identifiable code to one of the scan support member;
at least one transmitter disposed on one side of a bore of the imaging system, the at least one transmitter configured to transmit a beam incapable of effectively penetrating a scan object; and
a receiver disposed on the other side of the bore of the imaging system, the receiver configured to receive the beam transmitted by the at least one transmitter; and
a processing device configured to:
receive the distance measure from the identification device;
determine a distance from an interested location of the scan object to a scanning plane of the imaging system according to the distance represented by the machine identifiable code;
move the scan support member along a first axis to position the interested location at a desired point within the bore; and
determine a position of the scan object based on which of the beams associated with the at least one transmitter is detected by the receiver; and
move the scan support member along a second axis perpendicular to the first axis to position the interested location to a desired position within the bore.

2. The imaging system as claimed in claim 1, wherein the processing device determines the position of the scan object according to one or both of a position of a first transmitter whose transmitted beam is not blocked by the scan object, and a position of a second transmitter adjacent to the first transmitter and whose transmitted beam is blocked by the scan object.

3. The imaging system as claimed in claim 1, further comprising a guide member along which the at least one transmitter and the receiver can move in a direction perpendicular to the beam transmitted by the at least one transmitter.

4. The imaging system as claimed in claim 3, wherein the processing device determines the position of the scan object according to one or both of a position of the at least one transmitter at which the transmitted beam is not blocked by the scan object, and a next or a preceding position of the at least one transmitter at which the transmitted beam is blocked by the scan object.

5. The imaging system as claimed in claim 1, wherein the processing device is further configured to determine a distance from a center of an interested location of the scan object to a center of the bore.

6. The imaging system as claimed in claim 1, wherein a distance between neighboring transmitters is 3 mm to 5 mm, and a distance between neighboring receivers is 3 mm to 5 mm.

7. The imaging system as claimed in claim 1, wherein the beam transmitted by the at least one transmitter is a laser, an invisible light, or an ultrasonic wave.

8. The imaging system as claimed in claim 1, wherein the imaging system is a CT system, a PET system or an MRI system, and the at least one transmitter is a LED, a LD or a semiconductor laser.

9. The imaging system as claimed in claim 1, wherein:
the scan support member is one of: a scan support table, and
a scan support cradle located on a scan support table, wherein the scan support member shifting apparatus is configured to shift at least one of: the scan support table and the scan support cradle.

10. A method of positioning a scan object with respect to a bore of an imaging system, the method comprising:
identifying a first location of the scan object, said identifying comprising:
receiving a machine identifiable code on a scan support member, the machine identifiable code representing a distance from a position of the machine identifiable code to one end of the scan support member;
identifying a second location of the scan object said identifying comprising:
transmitting a beam incapable of effectively penetrating the scan object using at least one transmitter disposed on one side of a bore of the imaging system;
receiving the beam transmitted by the at least one transmitter and generating a received signal with a receiver disposed on the other side of the bore of the imaging system; and
and
positioning the scan object within the imaging system, said positioning comprising:
receiving the distance measure of the first location;
determining a distance from an interested location of the scan object to a scanning plane of the imaging system according to the distance represented by the machine identifiable code;
moving the scan support member along a first axis to position the interested location at a desired point within the bore of the imaging system; and
determining a position of the scan object based on which of the beams associated with the at least one transmitter is detected by the receiver; and
moving the scan support member along a second axis perpendicular to the first axis to position the interested location to a desired position within the bore of the imaging system.

11. The method as claimed in claim 10, wherein the position of the scan object is determined according to one or both of a position of a first transmitter whose transmitted beam is not blocked by the scan object, and a position of a second transmitter adjacent to the first transmitter and whose transmitted beam is blocked by the scan object.

12. The method as claimed in claim 10, wherein the at least one transmitter and the receiver can move in a direction perpendicular to the beams transmitted by the at least one transmitter.

13. The method as claimed in claim 12, wherein the position of the scan object is determined according to one or both of a position of the at least one transmitter at which the transmitted beam is not blocked by the scan object, and a next or a preceding position of the at least one transmitter at which the transmitted beam is blocked by the scan object.

14. The method as claimed in claim 10, further comprising:
   determining a distance from a center of the interested location of the scan object to a center of the bore.

15. The method as claimed in claim 14, further comprising:
   shifting the scan object according to the determined distance.

16. The method as claimed in claim 10, wherein a distance between neighboring transmitters is 3 mm to 5 mm, and a distance between neighboring receivers is 3 mm to 5 mm.

17. The method as claimed in claim 10, wherein the beam transmitted by the at least one transmitter is a laser, an invisible light, or an ultrasonic waves.

18. The method as claimed in claim 10, wherein the imaging system is a CT system, a PET system, or an MRI system and the at least one transmitter is a LED, a LD, or a semiconductor laser.

* * * * *